United States Patent
Chopra et al.

(10) Patent No.: US 9,707,413 B2
(45) Date of Patent: Jul. 18, 2017

(54) CONTROLLABLE ROTATING ULTRASOUND THERAPY APPLICATOR

(75) Inventors: Rajiv Chopra, Toronto (CA); Sean Donaldson, Toronto (CA); Cameron Mahon, Georgetown (CA)

(73) Assignee: Profound Medical Inc., Mississauga, ON ( * ) Notice: Subject to any disclaimer, the term of this patent is extended or adjusted under 35 U.S.C. 154(b) by 0 days.

(21) Appl. No.: 12/932,920

(22) Filed: Mar. 9, 2011

(65) Prior Publication Data

US 2011/0295161 A1    Dec. 1, 2011

Related U.S. Application Data

(60) Provisional application No. 61/311,853, filed on Mar. 9, 2010.

(51) Int. Cl.
*A61N 7/02* (2006.01)
*A61B 18/18* (2006.01)
(Continued)

(52) U.S. Cl.
CPC .......... *A61N 7/022* (2013.01); *A61B 18/1485* (2013.01); *A61B 18/1815* (2013.01);
(Continued)

(58) Field of Classification Search
CPC .. A61N 7/022; A61N 7/02; A61N 2007/0091; A61N 2007/0078;
(Continued)

(56) References Cited

U.S. PATENT DOCUMENTS

| 4,326,418 A | * | 4/1982 | Pell, Jr. ................. G10K 11/02 |
| | | | 310/322 |
| 4,880,011 A | | 11/1989 | Imade et al. |

(Continued)

FOREIGN PATENT DOCUMENTS

| WO | WO2011045695 A1 | 4/2011 |
| WO | WO2011091847 A1 | 8/2011 |

OTHER PUBLICATIONS

Chopra et al., Med. Phys., 27(6): 1281-1286, 2000.
(Continued)

*Primary Examiner* — Jennifer Dieterle
*Assistant Examiner* — Helene Bor
(74) *Attorney, Agent, or Firm* — Intrinsic Law Corp.

(57) ABSTRACT

An apparatus is disclosed for thermal therapy in a male prostate patient. The apparatus includes, in preferred embodiments, a long tubular element that is to be inserted into a patient's urethra so that a first tip end of it reaches up into the patient's diseased prostate. The elongated portion includes a narrow cylindrical tube within which an ultrasonic array is disposed along the long axis of the cylinder. Fluid is pumped into and out of a treatment zone of said patient as needed to control a temperature of a region in said treatment zone. A motorized driver is used to controllably rotate said elongated portion and the ultrasound array therein about the long axis of the apparatus so as to deliver acoustic energy to said diseased tissue. Various control and monitoring components may be used in conjunction with the present apparatus to design, control, and terminate the therapy.

13 Claims, 7 Drawing Sheets

(51) Int. Cl.
*A61B 18/14* (2006.01)
*A61F 7/12* (2006.01)
*A61B 18/00* (2006.01)
*A61B 90/00* (2016.01)
*A61B 17/00* (2006.01)
*A61N 7/00* (2006.01)

(52) U.S. Cl.
CPC .................. *A61F 7/12* (2013.01); *A61N 7/02* (2013.01); *A61B 2017/00274* (2013.01); *A61B 2018/00011* (2013.01); *A61B 2018/00023* (2013.01); *A61B 2018/00517* (2013.01); *A61B 2018/00547* (2013.01); *A61B 2090/374* (2016.02); *A61B 2090/378* (2016.02); *A61N 2007/0078* (2013.01); *A61N 2007/0091* (2013.01)

(58) Field of Classification Search
CPC ............ A61B 18/1485; A61B 18/1815; A61B 2018/00547; A61B 2017/00274; A61B 2018/00517; A61B 2090/378; A61B 2018/00011; A61B 2090/374; A61B 2018/00023; A61F 7/12
USPC ....................... 600/411, 462, 439; 606/96, 27
See application file for complete search history.

(56) References Cited

U.S. PATENT DOCUMENTS

| | | | |
|---|---|---|---|
| 5,295,484 A | 3/1994 | Marcus et al. | |
| 5,593,381 A | 1/1997 | Tannenbaum et al. | |
| 5,593,415 A | 1/1997 | Adrian | |
| 5,601,526 A | 2/1997 | Chapelon et al. | |
| 5,620,479 A | 4/1997 | Diederich | |
| 5,647,361 A | 7/1997 | Damadian | |
| 5,666,954 A | 9/1997 | Chapelon et al. | |
| 5,733,315 A | 3/1998 | Burdette et al. | |
| 6,050,943 A | 4/2000 | Stayton et al. | |
| 6,077,257 A | 6/2000 | Edwards et al. | |
| 6,100,626 A * | 8/2000 | Frey et al. | 310/334 |
| 6,113,546 A * | 9/2000 | Suorsa et al. | 600/459 |
| 6,122,551 A | 9/2000 | Rudie et al. | |
| 6,241,725 B1 | 6/2001 | Cosman | |
| 6,254,553 B1 | 7/2001 | Lidgren et al. | |
| 6,379,320 B1 | 4/2002 | Lafon et al. | |
| 6,393,314 B1 * | 5/2002 | Watkins et al. | 600/411 |
| 6,418,337 B1 | 7/2002 | Torchia et al. | |
| 6,432,067 B1 | 8/2002 | Martin et al. | |
| 6,490,488 B1 | 12/2002 | Rudie et al. | |
| 6,500,121 B1 | 12/2002 | Stayton et al. | |
| 6,516,211 B1 | 2/2003 | Acker et al. | |
| 6,522,142 B1 | 2/2003 | Freundlich | |
| 6,537,306 B1 | 3/2003 | Burdette et al. | |
| 6,542,767 B1 | 4/2003 | McNichols et al. | |
| 6,559,644 B2 | 5/2003 | Freundlich et al. | |
| 6,582,381 B1 | 6/2003 | Marantz et al. | |
| 6,589,174 B1 | 7/2003 | Chopra et al. | |
| 6,618,608 B1 | 9/2003 | Watkins et al. | |
| 6,618,620 B1 | 9/2003 | Freundlich et al. | |
| 6,623,430 B1 | 9/2003 | Stayton et al. | |
| 6,671,535 B1 | 12/2003 | McNichols et al. | |
| 6,692,450 B1 | 2/2004 | Coleman | |
| 6,692,518 B2 | 2/2004 | Carson | |
| 6,735,461 B2 | 5/2004 | Vitek et al. | |
| 6,746,465 B2 | 6/2004 | Diederich et al. | |
| 6,755,849 B1 | 6/2004 | Gowda et al. | |
| 6,818,012 B2 | 11/2004 | Ellingboe | |
| 6,823,216 B1 | 11/2004 | Salomir et al. | |
| 7,044,960 B2 | 5/2006 | Voorhees et al. | |
| 7,135,029 B2 | 11/2006 | Makin et al. | |
| 7,167,741 B2 | 1/2007 | Torchia et al. | |
| 7,229,411 B2 | 6/2007 | Stayton et al. | |
| 7,233,820 B2 | 6/2007 | Gilboa | |
| 7,344,529 B2 | 3/2008 | Torchia et al. | |
| 7,404,809 B2 | 7/2008 | Susi | |
| 7,473,224 B2 | 1/2009 | Makin | |
| 7,771,418 B2 | 8/2010 | Chopra et al. | |
| 7,806,892 B2 | 10/2010 | Makin et al. | |
| 7,951,182 B2 | 5/2011 | Stelea et al. | |
| 7,993,289 B2 | 8/2011 | Quistgaard et al. | |
| 8,021,406 B2 | 9/2011 | Cazzini et al. | |
| 8,025,688 B2 | 9/2011 | Diederich et al. | |
| 8,066,641 B2 | 11/2011 | Barthe et al. | |
| 8,244,327 B2 | 8/2012 | Fichtinger et al. | |
| 2001/0003798 A1 * | 6/2001 | McGovern et al. | 606/41 |
| 2003/0004439 A1 | 1/2003 | Pant et al. | |
| 2003/0018266 A1 | 1/2003 | Makin et al. | |
| 2003/0069502 A1 | 4/2003 | Makin et al. | |
| 2003/0092988 A1 | 5/2003 | Makin | |
| 2006/0206105 A1 * | 9/2006 | Chopra et al. | 606/27 |
| 2006/0241368 A1 * | 10/2006 | Fichtinger et al. | 600/407 |
| 2006/0241442 A1 | 10/2006 | Barthe et al. | |
| 2007/0021648 A1 * | 1/2007 | Lenker | A61M 25/0097 600/29 |
| 2007/0106157 A1 | 5/2007 | Kaczkowski et al. | |
| 2007/0239062 A1 | 10/2007 | Chopra et al. | |
| 2008/0242970 A1 | 10/2008 | Minagawa et al. | |
| 2009/0143775 A1 | 6/2009 | Rizoiu et al. | |
| 2009/0171185 A1 | 7/2009 | Chou et al. | |
| 2010/0256480 A1 * | 10/2010 | Bottomley et al. | 600/411 |
| 2011/0034833 A1 | 2/2011 | Chopra et al. | |
| 2011/0144524 A1 | 6/2011 | Fish et al. | |
| 2011/0282156 A1 * | 11/2011 | Lenker | A61B 17/3439 600/208 |

OTHER PUBLICATIONS

Chopra et al., IEEE Transactions on Ultrasonics, Ferroelectrics, and Frequency Control, 50(7):881-889, 2003.
Diederich et al., Med. Phys., 31(2):405-413, 2004.
Kowalski et al., Phys. Med. Biol., 48:633-651, 2003.
Lafon et al., Ultrasonics, 36:683-687, 1998.
Lafon et al., Ultrasound Med. Biol., 30(1):113-122, 2004.
McNichols et al., Lasers Surg. Med., 34:48-55, 2004.
Ross et al., Phys. Med. Biol., 49:189-204, 2004.
Smith et al., Int. J. Hyperthermia, 17(3): 271-282, 2001.
Vanne et al., Phys. Med. Biol., 48: 31-43, 2003.
H. L. Liu et al., "Pilot point temperature regulation for thermal lesion control during ultrasound thermal therapy", Med. Biol. Eng. Comput., 2004, p. 178-188, vol. 42.
M. Burtnyk et al., "Quantitative analysis of 3-D conformal MRI-guided transurethral ultrasound therapy of the prostate: Theoretical simulations", International Journal of Hyperthermia, Mar. 2009, p. 116-131, vol. 25, No. 2.
European Patent Office, "Extended European Search Report—Application No. 12835517.9", Oct. 27, 2015, EPO.

* cited by examiner

CONTROLLABLE ROTATING ULTRASOUND THERAPY APPLICATOR

RELATED APPLICATIONS

The present application is related to and claims priority under 35 USC §120 to U.S. Provisional Application No. 61/311,853, bearing the present title, filed on Mar. 9, 2010, which is hereby incorporated by reference.

TECHNICAL FIELD

The present application relates to ultrasound therapy systems, and particularly to the construction and operation of an array of ultrasound sources for use in such systems.

BACKGROUND

Ultrasonic transducers have been employed in ultrasound therapy systems to achieve therapeutic heating of diseased and other tissues. Phased ultrasound arrays of transducers operating to form a beam of ultrasonic energy cause a conversion of sound to thermal energy in the affected tissue areas or treatment volumes, and a subsequent beneficial rise in the temperature in the treatment volumes. With proper monitoring of the heating effect, ultrasound therapy systems can be used to treat harmful cells and to controllably destroy cancerous tumors.

As known to those skilled in the art, ultrasonic transducers are constructed and operated to take electrical power and produce ultrasound energy waves from a surface of a transducer element in a process generally referred to as transduction. The nature and extent of the transduction depends on the material used to construct the transducers, transducer geometry, and the electrical input to the transducers. A common material used in construction of ultrasound transducers is piezo-electric transducer crystal material (lead zirconate titanate, PZT) which comes in several forms.

Various designs for ultrasonic array systems have been used in the present field of art. The present disclosure will not provide a detailed exposition of the prior arrays. Ultrasound array design can be challenging, and improvements to such designs would improve the effectiveness, safety and cost to manufacture of such arrays.

SUMMARY

Embodiments hereof are directed to systems and methods for providing an image-guided thermal therapy system including an ultrasonic array of transducers. In some respects, the present disclosure provides improved ultrasonic array designs to achieve better thermal therapy in such situations as trans-urethral prostate cancer therapy.

Aspects of the present disclosure provide a system with a computer controlled or microprocessor controlled RF driving unit that electrically drives piezo electric ultrasound transducer elements in an ultrasound therapy system as well as ways for coupling the arrays to a power source which can controllably power the elements of the arrays.

Some embodiments are directed to apparatus for thermal therapy in a patient, comprising an elongated cylindrical portion having a first end thereof sized and configured for insertion into a male urethra; an array of ultrasonic sources disposed within said elongated cylindrical portion and substantially arranged along an axis of said elongated cylindrical portion proximal to said first end of the elongated cylindrical portion, the ultrasonic sources being electrically driven to provide thermal therapy in said patient; a plurality of electrical conductors, respectively coupled to a plurality of said ultrasonic sources of said array, said conductors providing power and control signals to said respective plurality of ultrasonic sources and driving said sources to deliver acoustic emissions of respective frequency and power depending on the respective power and control signals; a rotational mechanical coupling proximal to a second end of said elongated cylindrical portion, sa id rotational mechanical coupling designed and arranged to permit mechanical rotation of said elongated cylindrical portion about said axis thereof; and at least one fluid conduit running through said rotational mechanical coupling permitting a fluid to circulate into and then out of said apparatus by flowing from said second end towards said first end of the elongated cylindrical portion and back again.

Other embodiments are directed to method for thermal therapy in a patient, comprising providing a thermal therapy apparatus having an elongated portion thereof and preparing said apparatus for insertion into a urethra of said patient; inserting said elongated portion into said patient's urethra by translating at least a portion of said apparatus along an axis of said apparatus; delivering a plurality of electrical power and control signals to a corresponding plurality of ultrasonic elements disposed within said elongated portion, said electrical power and control signals providing at least frequency and power control driving signals to their respective ultrasonic elements; once the insertion step above has been accomplished satisfactorily, programmably rotating said apparatus about an axis of rotation, which axis of rotation is substantially the same as or parallel to said axis of said apparatus and its elongated portion; delivering sufficient ultrasonic energy from said plurality of ultrasonic sources into a diseased volume of said patient to effect a clinically-significant change in said diseased volume; and monitoring a result of said step of delivering said ultrasonic energy, including monitoring a temperature of said diseased volume.

BRIEF DESCRIPTION OF THE DRAWINGS

For a fuller understanding of the nature and advantages of the present invention, reference is be made to the following detailed description of preferred embodiments and in connection with the accompanying drawings, in which.

DETAILED DESCRIPTION

As discussed above, improved ultrasound thermal therapy applicators can improve treatment of diseases such as tumors, and for example as used in trans-urethral treatment of prostate cancers in male patients.

Figure 1:
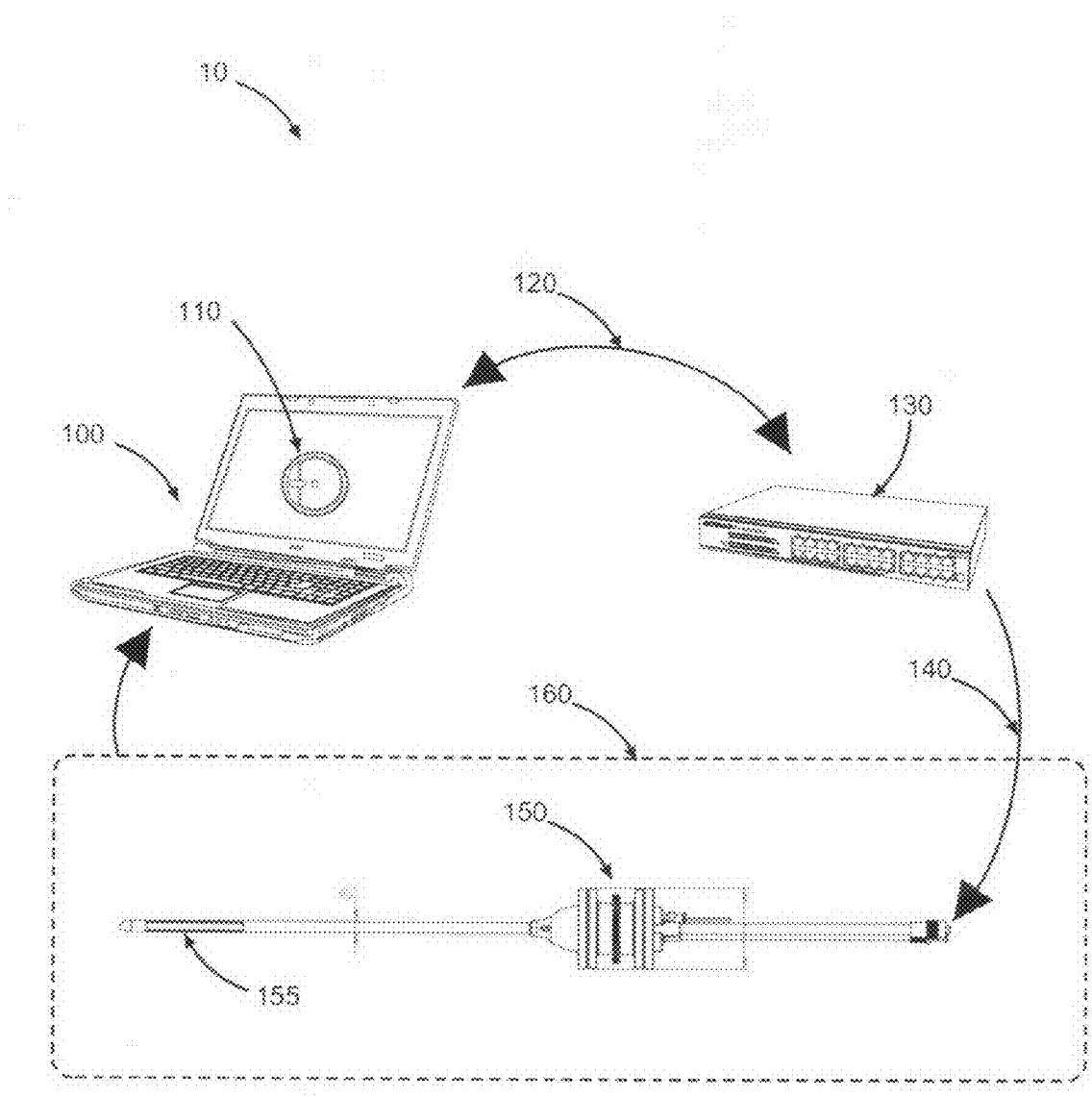
FIG. 1 illustrates an exemplary system for providing image-guided ultrasound therapy to a patient.

FIG. 1 illustrates an exemplary system 10 for providing image-guided ultrasound therapy to a patient. The simplified illustration shows a master computer 100, such as a portable PC, workstation, or other processing device having a processor, memory, and coupled to some input/output apparatus. Master computer 100 may include a display and may support a user interface 110 to facilitate control of and observation of the thermal therapy treatment process.

Master computer 100 is adapted for coupling to other systems and components through a computer interface connector 120. Connection 120 carries data and information to and from master computer 100 and may comprise standard or special-purpose electrical wiring connection cables, such as serial connection cables or the like. Also, connection 120 may be achieved wirelessly as known to those skilled in the art of wireless communication, and may further be achieved by way of multiple connections, over a network, or by another suitable method.

In some embodiments, master computer 100 is coupled through connection 120 to a power control unit 130. Power control unit 130 may be implemented as a stand-alone hardware apparatus but may be implemented as a part of master computer 100, e.g., by being built onto a special card in a computer or server system that accommodates such hardware components.

Power control unit 130 may specifically include at least a processor adapted for processing machine or program instructions, which may be provided to the processor from another component of system 10 and may be stored on a memory device in power control unit 130. Circuitry including analog and/or digital circuitry may be operated within power control unit 130 so as to determine an output power to one or more ultrasound therapy transducer elements in an ultrasound therapy apparatus 150.

In some embodiments, power control unit 130 may deliver controlled electrical driving signals to a plurality of ultrasound transducer elements (e.g., PZT array elements) in ultrasound therapy apparatus 150. The driving signals may be controlled to deliver a programmed amount of power to each element or to groups of elements of therapy apparatus 150. The driving signals may also be controlled so as to provide a determined driving voltage, current, amplitude, waveform, or frequency to said ultrasonic transducers of therapy apparatus 150. Such electrical driving signals are carried from power control unit 130 to the ultrasound therapy apparatus 150 over suitable wires, cables, or buses 140. Appropriate plug interfaces or connectors may be included so as to mate the various ends of the connectors or buses to and from their associated components.

In operation, ultrasound therapy apparatus 150 includes a portion 155 that is inserted into a portion of a patient's body to deliver a suitable dose of ultrasound energy to tissue in a diseased region of the patient's body.

The patient and the ultrasound therapy apparatus 150 are generally disposed in an imaging volume 160 such as a magnetic resonance imaging (MRI) apparatus, which can provide real-time images of the relevant parts of the patient, e.g., the treatment volume to master computer 100 or display and user interface 110. In some embodiments, real-time monitoring of the thermal therapy is performed so that a clinical operator can monitor the progress of the therapy within the treatment volume or diseased tissue. Manual or automated changes can be made to the power signals from power control unit 130 based on input from the results and progress of the treatment.

The feedback and coupling of the treatment system components to the control components in system 10 can be used to ensure that an optimum radio frequency (RF) power signal is provided to each element of an ultrasound array 155 used in treatment of diseased tissues. Some examples include treatment of prostate cancer tumors in male patients using MRI guided ultrasound therapy applications.

RF power control unit 130 may include separate circuit cards having individual processors, amplifiers, filters and other components to achieve the desired driving power output to the elements of ultrasound array 155 of ultrasound treatment apparatus 150. Alternatively, a single processor may be employed to control the behavior of the various power channels to each array element.

Figure 2:
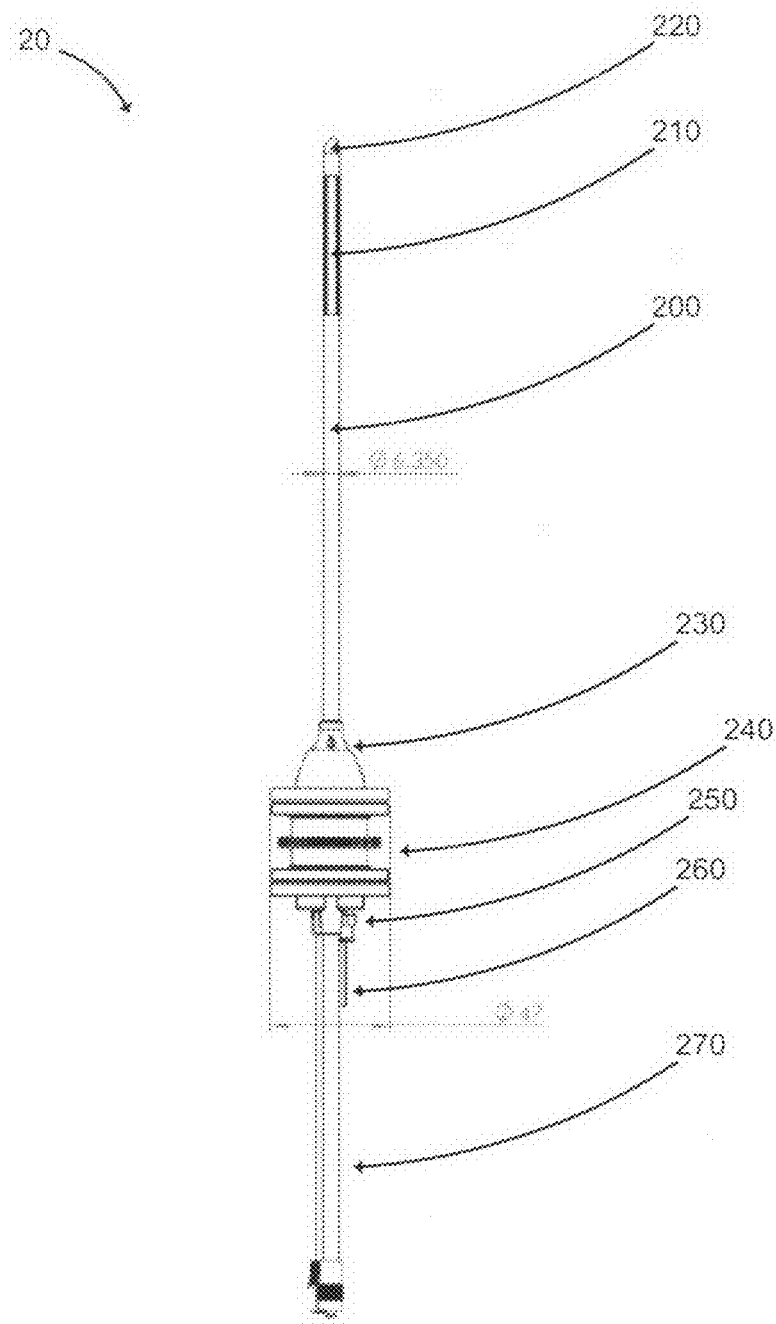
FIG. 2 illustrates an exemplary design of an elongated ultrasound thermal therapy applicator.

FIG. 2 illustrates an exemplary ultrasound therapy applicator design. Applicator 20 includes an elongated shaft portion 200, which can be inserted into a body cavity proximal to a diseased tissue region of a patient. In some instances, elongated shaft portion 200 (or a portion thereof) may be inserted into the urethra of a male patient to treat diseased tissue such as cancerous tissue of the male prostate. The insertion of applicator 20 into the patient is done by pressing the applicator 20 into an appropriate channel, optionally using image guidance such as MRI or X-ray guidance to monitor the movement of applicator 20 within the patient.

The applicator 20, or typically the elongated shaft portion 200, are inserted into the patient until the transducer array 210 reaches an area proximal to the diseased tissue volume or target volume for the thermal therapy. In this way, when power is provided to the transducer array 210 it will cause a controlled heating of the diseased tissue volume to treat the disease condition or affect some other desired outcome. Tip 220, as will be discussed below, may be constructed of blunt smooth material such as a polymer or metal material to assist in easy reduced friction insertion and movement of applicator 20 into the patient. In some embodiments, this design minimizes frictional stress on the interior walls of the patient's urethra.

A transition portion 230 of applicator 20 is flared or bulbous in shape and provides a safety zone that prevents unwanted portions of apparatus 20 from entering into the patient's body.

Flanged portions of transition portion 230 allow for easier manipulation of applicator 20 and mechanical control of the same as will be described below in further detail. The portion 230 can act as a handle for holding the applicator and may be constructed of an optically transparent material such as clear plastic. This can allow viewing of the interior of the apparatus in some situations to determine if any gas (air) bubbles have been trapped in the fluid circuit portion of the apparatus. The gas can then be vacated to minimize or avoid interference in the transmission of ultrasound energy from the transducer system or interference with the cooling fluid flow within the body of the system. The flanges can also provide a mechanical means for holding applicator 20 in place within a bearing system or rotation and translation driver used to move and rotate applicator 20 during operation.

A geared element 240 provides a mechanically-compatible actuation means for rotating applicator 20 within the patient's body so that array 210 is properly and controllably rotated about the long axis of shaft 200 to treat a volume of tissue up to a complete 360 degree rotation volume surrounding the axis of shaft 200 if desired. In some embodiments, a motor is adapted for driving the gear 240 of applicator 20 to provide such rotation of the applicator within the patient about the long axis of the applicator.

Mechanical interfaces 250 allow coupling of fluid intake and outtake connections to applicator 20 so that temperature control fluid can be passed into and out of the applicator 20. For example, in situations where cooling of the applicator itself or surrounding tissue in needed, the fluid can be applied to these interfaces optionally using standard fluid hook-up connectors and tubing 270. Also, electrical wiring 260 or micro-buses can be passed through interfaces 250 to provide electrical driving power to the elements of transducer array 210 and to receive sensor signals or other signals and data from the components of applicator 20. Again, standard electrical connectors may be used to interface outside power and control systems with the internal electrical elements of applicator 20.

In operation, applicator 20 may be placed with tip 220 proximal to an aperture in the patient's body and with the long axis of shaft 200 substantially aligned with a cavity or channel (e.g., the urethra) of the patient for insertion therein. The applicator 20 is then automatically or manually or by a combination of the two inserted into the patient's body, beginning with tip 220 end of shaft 200. When the applicator 20 is sufficiently inserted into the patient's body (e.g., using image guided translation motor stages) the translation of applicator 20 is secured. Then, a computer-controlled thermal therapy procedure is undertaken, with applicator 20 being rotated about its long axis within the patient's body so that transducer array 210 provides a therapeutic energy field such as an ultrasonic field of known strength and nature to treat the diseased tissue proximal to array 210. When the thermal therapy is completed, power to ultrasound array 210 is secured and applicator 20 is retracted from the patient substantially along the long axis of the applicator, in substantially the reverse direction as it was inserted.

Figure 3:
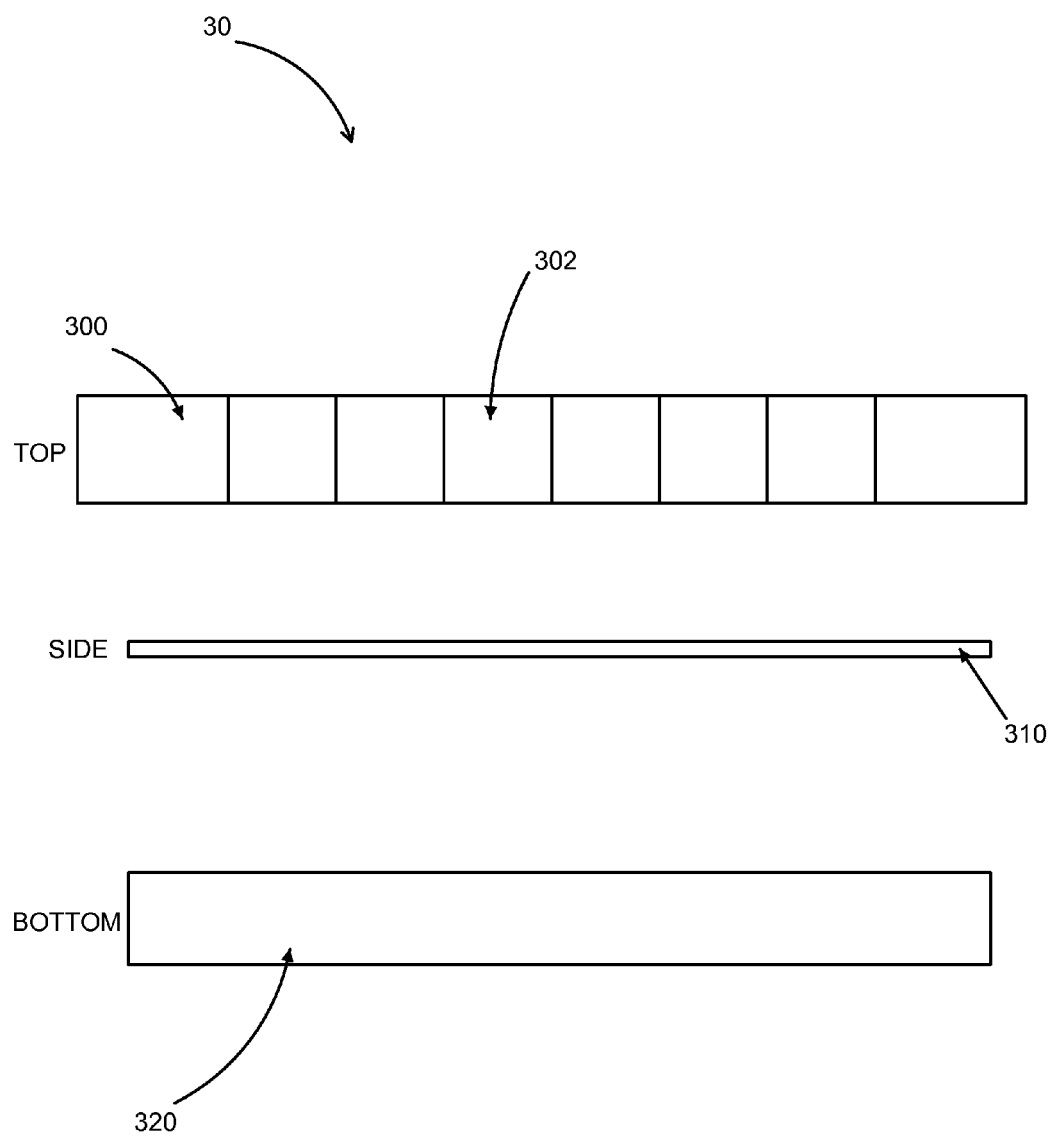
FIG. 3 illustrates an exemplary ultrasonic array for use in an ultrasound therapy system.

FIG. 3 illustrates an exemplary design for the transducer array (such as array 210 of FIG. 2). An ultrasonic array 30 is shown as it appears from the "top" face thereof at view 300. Note that in the present illustration the "top" face is the face of the array normally facing into the center of the applicator shaft and away from the patient's body. The same array is shown from the side in view 310. The opposing or "bottom" view of the array is shown in view 320, and is the face of the array which is outwardly directed at the patient's treatment volume and away from the applicator. It is seen that in this exemplary embodiment the ultrasonic array is constructed from a substantially flat or relatively planar material. This may be a PZT-based material as is generally known to those skilled in the art. In some embodiments the material may comprise K320 from Piezo Technologies of Indianapolis, Ind. USA. Alternately, it may be made of PZ52 of similar material from Ferroperm Piezoceramics of Kvistgaard, Denmark. The array and its elements may be designed and arranged to have a pre-determined optimal resonance frequency, for example 4 MHz, or other central frequency for best penetration and power delivery to the diseased volume of tissue, in some embodiments, along with a third harmonic at 13 MHz as well.

According to the present embodiment, the front face of transducer array 30 is cut into a plurality of individual array elements, e.g., 302. The individual elements 302 may or may not all be of the same shape and size. The dimensions given in the figure are merely illustrative. In certain embodiments, the elements 302 are substantially rectangular or square in shape and provide an ultrasonic energy field proximal to the face of elements 302 as dictated by the design, material and driving signals for the elements 302. The elements 302 of array 30 may be driven in a programmed way as discussed in other applications by the present inventors and assignee to create an overall ultrasonic therapeutic energy field within a controlled volume of tissue in a patient. The array 30 mounted to the rest of the therapy applicator may be rotated about the long axis of array 30 so as to provide treatment to a volume around array 30 as needed.

Both the front face 300 and the back face 320 of array 30 are silvered to permit delivery of driving power signals to and grounding of the elements of array 30. The ends and edges (shown in 310) of array 30 may be left unsilvered. In this way some or all of elements 302 may be powered by an appropriate power source.

In some embodiments, one or both elements at the ends of array 30 may be "dummy" elements that are not substantially driven or used for the actual thermal therapy in operation of the device.

Figure 4:
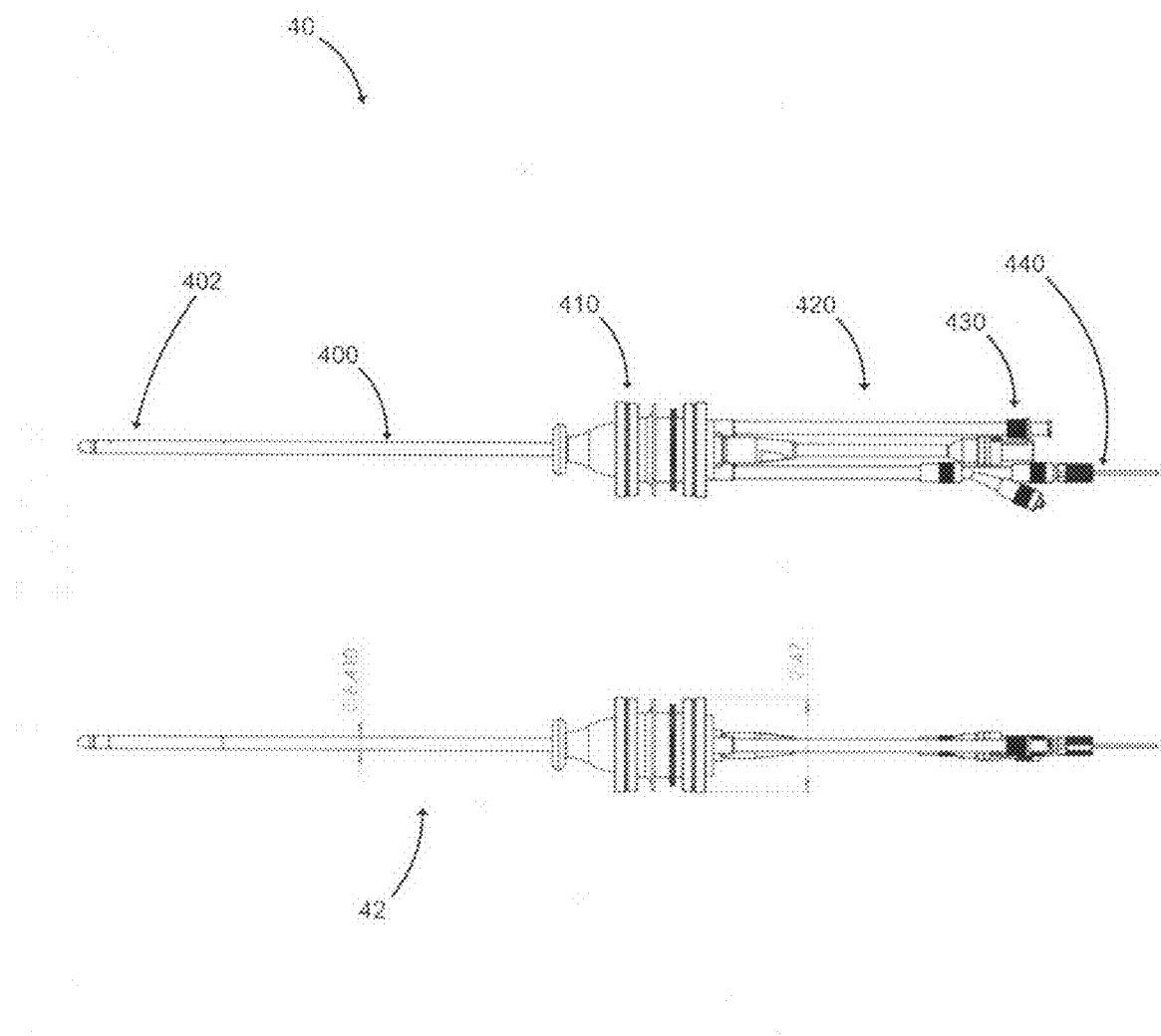
FIG. 4 illustrates two views of an elongated ultrasonic thermal therapy applicator according to exemplary embodiments hereof.

FIG. 4 illustrates two views 40 and 42 of an illustrative ultrasound therapy applicator device, showing the exemplary arrangement of the connectors and transitional mechanical elements thereof with respect to the elongated shaft and transducer array portions as described above. An elongated portion 400 is designed for insertion into a male urethra, optionally by applying an acoustically-compatible lubricant or disinfecting liquid or gel to an exterior of elongated portion 400. Ultrasound elements are arranged within and running along a portion near the tip 402 of elongated applicator 400. This is the part of the apparatus which is inserted into the patient's body until it is substantially situated within a volume of diseased tissue (e.g., the prostate) and from which the ultrasonic thermal energy is emitted into the diseased tissue.

The elongated portion is supported by and secured to one or more flanged elements of the applicator body, which in a preferred embodiment act as bearings 410 or gear elements to assist in rotating the applicator about its long axis once the applicator's tip is at the desired depth within the patient. In some aspects, a motorized driver as described elsewhere by the present applicant is used to mechanically rotate and/or translate the apparatus.

For example, in a preferred embodiment, the applicator 40, 42 is inserted into a patient who is lying on and secured to a bed, table, or platform. Once inserted to the proper position in the patient so that the ultrasonic array in portion 402 of the applicator is proximal to the diseased tissue, a rotational stepper motor or other piezo-electric driver is used to mechanically turn the apparatus and hence the ultrasonic array of the apparatus about its axis so as to sonicate the diseased tissue (prostate) to the desired degree using computer-controlled power, frequency or other electrical driving signals delivered to the elements of the array at 402.

As discussed elsewhere in this disclosure, electrical and mechanical (e.g., fluid) connections are made from portions of the applicator outside the patient's body to portions of the applicator inserted into the patient's body. Preferably, such mechanical and electrical connections employ physically compact components to reduce the discomfort felt by the patient and to reduce the chances of strain on the patient's healthy organs (e.g., urethra). Accordingly, in an embodiment, fluid conduits 420 into and out of the patient are provided with appropriate transitional or coupling ends and deliver electrical or fluid content to and from the elongated portion 400 and proximal to tip end 402 of the apparatus. Further coupling using fluid couplings 430 and electrical couplings 440 are provided, and these couplings are connected to corresponding parts of the fluid circuit pumping fluid into the applicator and out of the same and electrical circuits delivering power and control capability to the system, respectively.

Figure 5:
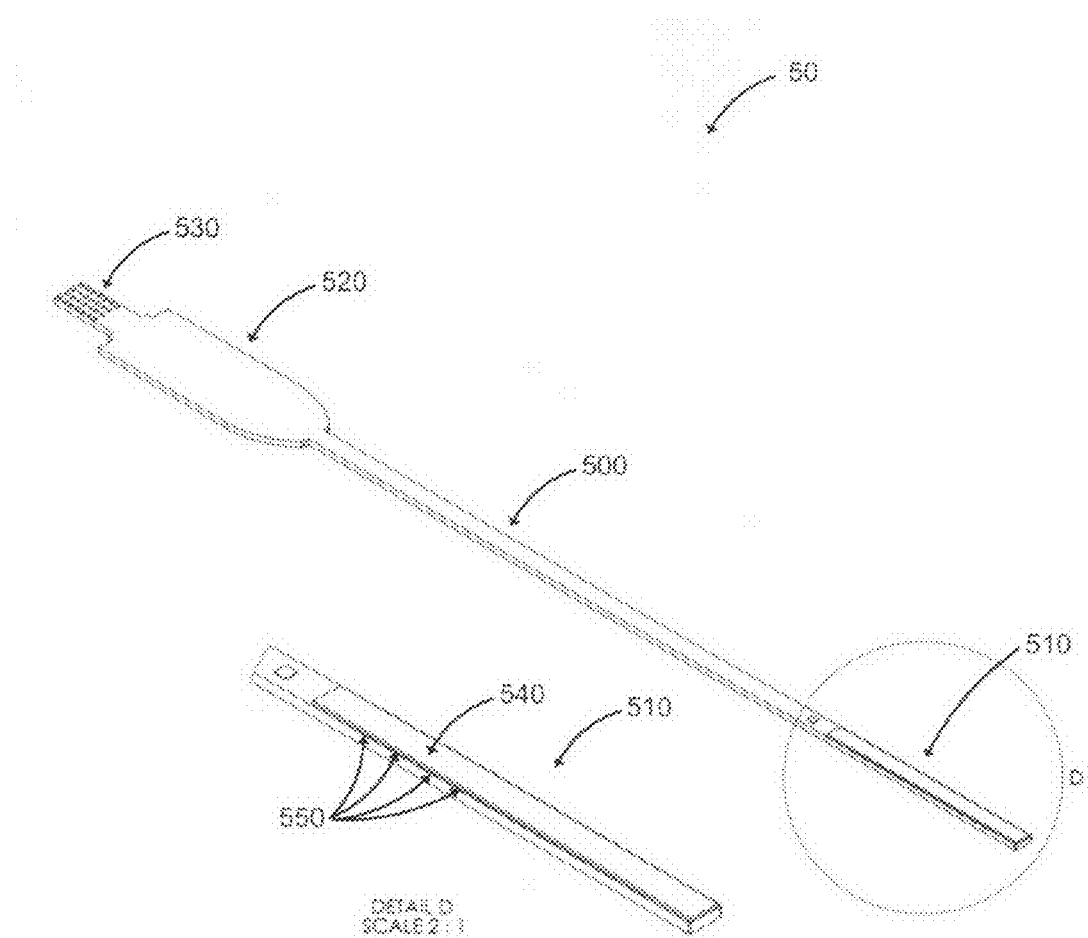
FIG. 5 illustrates an exemplary sequence for a method used in ultrasound thermal therapy.

FIG. 5 illustrates an exemplary internal view of the transducer support and assembly member 50, on which the ultrasonic array is supported and on which the circuitry for driving the elements of the array are mounted. In the present embodiment, an elongated substantially flattened and paddle-like shaped support member 50 has a long shaft section 500. Ultrasonic array 510 is disposed near a first end of said shaft section, and array 510 may be attached, fixed, mounted or adhered to said long section 500 by any means convenient or effective for a particular application and geometry.

A wider section 520 extends from a second end of elongated section 500 and is placed within a transitional portion of the therapy applicator and is generally not inserted into the patient's body. An electrical connection 530 is provided for connecting to the outside electrical power drive and control system.

In some embodiments the support and assembly member 50 is made of or on or includes a printed circuit board (PCB) material. On the PCB, thin electrical connections are printed and run from electrical connector 530 up the shaft 500 to power the elements of transducer array 510.

A detail "D" of the array 510 end of the system is shown below in the same drawing. The common ground "bottom" face 540 of the transducer array is shown, as are several connection points 550 to the "top" face of the individual transducer elements on the opposing face of array 510. The individual wiring can be accomplished by placement of the array onto the PCB support member and soldering of connections between the PCB circuitry and the individual array elements so as to allow individual power and control of the same.

An inter-metallic bond or epoxy connection points can be used to couple the transducer elements to the PCB lines. The connection points form "pads" of a finite thickness. These pads cause the surface of the PCB and the surface of the transducers to be separated (e.g., by a thickness of about 0.003 inch). 3-oz copper pad connection points will provide approximately a 0.0034 inch air gap. The separation is air-filled or gas-filled so as to provide an "air backing" to the transducer array 510 so that the array directs its energy outwardly from the "bottom" face thereof, facing the patient, as opposed to radiating its energy through the top face or another direction. This spacing of the array and the support structure 500 is a design feature that eliminates the need for using a spacer to provide the air-backing in some embodiments. It is noted that the present exemplary dimensions and arrangements are given for the sake of illustration, and are not limiting, so that one of skill in the art would appreciate other forms and sizes and arrangements accomplishing substantially same or similar ends in similar ways.

Figure 6:
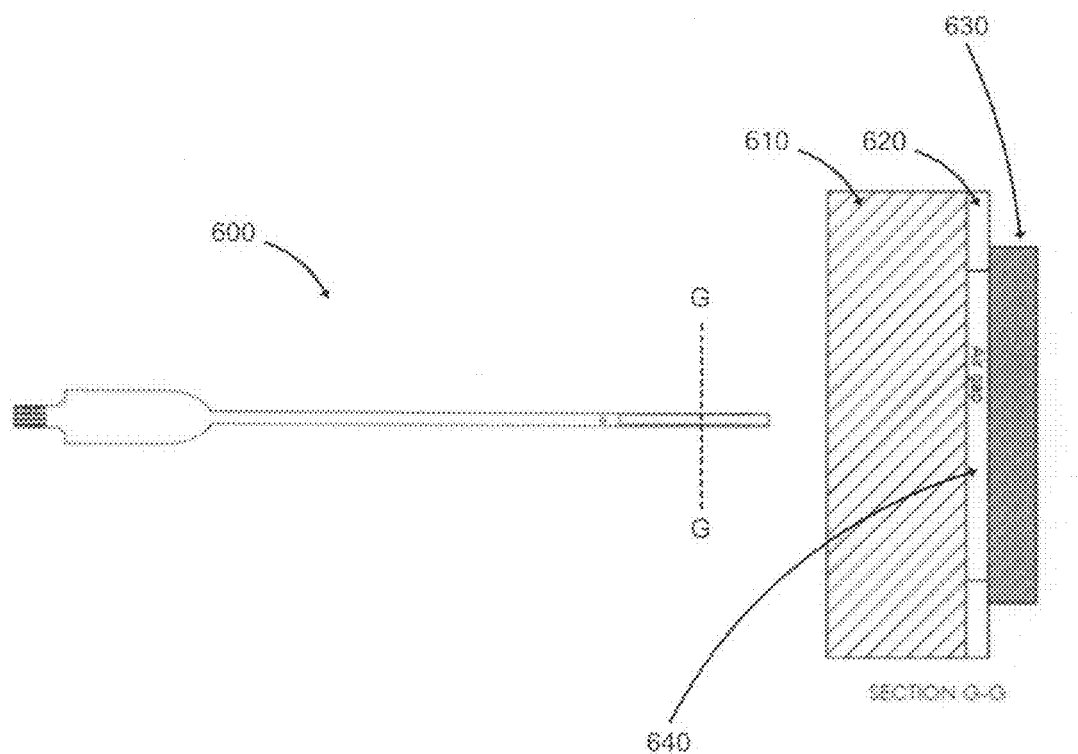
FIG. 6 illustrates a view of the circuit support member such as a PCB support member.

FIG. 6 illustrates a view of the circuit support member 600 such as the PCB support member described above. A section G-G is shown to the right to illustrate an exemplary arrangement of the silvered transducer element 630, which is coupled to the PCB stalk material 610 by copper or other conducting pads 620. The pads 620 are of a thickness as described above to provide a suitable air gap 640 so that the transducers 630 are properly air-backed for transmitting ultrasonic energy from the bottom face of the elements 630 (to the right in FIG. 6) towards the diseased tissue of the patient.

Figure 7:
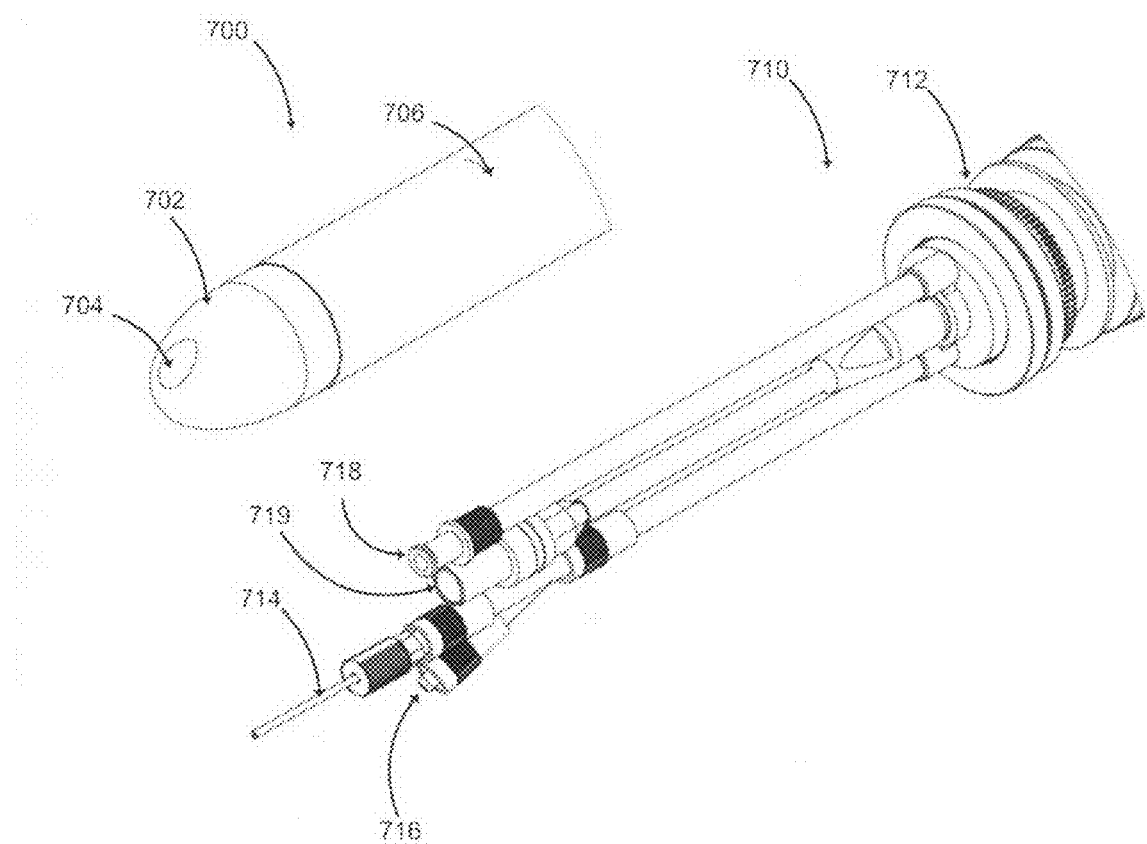
FIG. 7 illustrates exemplary designs of two ends of an ultrasound treatment applicator, one for insertion into a treatment volume of a patient's body and the other for coupling to mechanical and electrical components of the treatment system.

FIG. 7 illustrates exemplary designs of two ends of an ultrasound treatment applicator.

At one end 700 of the applicator, as discussed earlier, is a tip portion 702 coupled to the inserted end of the elongated shaft member 706 of the applicator. In some embodiments, a fiber optic or other temperature sensor is placed at or near the tip of the applicator for sensing the temperature in or near the tip of the applicator.

In some embodiments, a hole 704 or small orifice is disposed at or near the leading end of tip 702. The hole allows for drainage of fluid, e.g. urine that may collect in the patient near the tip end of the applicator. This can reduce the swelling or pressure in the patient near the treatment zone during a thermal therapy procedure. The fluid drained from the patient through hole 704 may be carried in a tube or channel down the length of the applicator apparatus to the opposite end of the applicator and outside the patient at exterior end 710 of the applicator.

End 710 of the thermal therapy applicator includes a catheter 714 in fluid communication with the hole 704 in tip 702. This catheter delivers fluid (e.g., urine) drained from the patient's body to a suitable retainer or receiving volume. The drained fluid can be monitored for blood, drugs, temperature, or other attributes. A valve or shut-off apparatus may be included in-line with catheter 714 to control the flow of fluid in or out of the catheter. In some embodiments fluid may be delivered in to the patient's body, including drug delivery to the patient near the tip 702 of the applicator.

The present invention should not be considered limited to the particular embodiments described above. Various modifications, equivalent processes, as well as numerous structures to which the present invention may be applicable, will be readily apparent to those skilled in the art to which the present invention is directed upon review of the present disclosure.

We claim:

1. An apparatus for thermal therapy in a patient, comprising:
    an elongated cylindrical body having a first end thereof sized and configured for insertion into a male urethra;
    an array of ultrasonic sources disposed within said elongated cylindrical body and arranged along an axis of said elongated cylindrical portion proximal to said first end of the elongated cylindrical portion, the ultrasonic sources being electrically driven to provide thermal therapy in said patient;
    a transition body portion directly connected to a second end of said elongated cylindrical body, said transition body portion including a flared portion that limits a depth of said insertion into said male urethra and a flanged portion, said flanged portion disposed between said second end and said flared portion;
    an elongated printed circuit board disposed in said elongated cylindrical body and extending from said first end of said elongated cylindrical body to said transition body portion such that a portion of said elongated circuit board is disposed outside said depth of said insertion, said circuit board including a plurality of printed circuit lines respectively coupled to a plurality of said ultrasonic sources of said array, said circuit lines providing power and control signals to said respective plurality of ultrasonic sources and driving said sources to deliver acoustic emissions of respective frequency and power depending on the respective power and control signals, said plurality of circuit lines on said circuit board being electrically and mechanically coupled to said plurality of ultrasonic sources of said array by way of respective conducting epoxy points or pads of finite thickness so as to cause a gas-filled separation between back sides of said ultrasonic sources and said circuit board therefore so as to cause an outward radiation of ultrasonic energy from an outward face of said ultrasonic sources, wherein said epoxy points or pads are disposed between said ultrasonic sources and said circuit board, said gas-filled separation having a width determined by said thickness of said epoxy points or pads and a height determined by a distance between adjacent epoxy points or pads;

a rotational mechanical coupling directly connected to said flanged portion that supports and secures said elongated cylindrical portion, said rotational mechanical coupling further designed and arranged to permit mechanical rotation of said elongated cylindrical portion about said axis thereof and including a geared wheel configured to mechanically engage a rotational driver to convert a rotational movement of said driver to a corresponding rotational movement of said geared element; and at least one fluid conduit running through said rotational mechanical coupling permitting a fluid to circulate into and then out of said apparatus by flowing from said second end towards said first end of the elongated cylindrical portion and back again.

2. The apparatus of claim 1, further comprising an orifice proximal to said first end of said elongated cylindrical portion, the orifice arranged to draw a body fluid from an interior of said patient, through said elongated cylindrical portion and out of the apparatus.

3. The apparatus of claim 1, said array of ultrasonic sources being disposed on an elongated support plate having a first elongated portion shaped and sized to fit within an interior cavity in said elongated cylindrical portion proximal to said first end and a second widened portion having a flattened and paddle-like shape proximal to said second end including a plurality of printed connection points or pads.

4. The apparatus of claim 3, said plurality of printed circuit electrically connected at one end thereof to said ultrasonic sources and electrically connected at another end thereof to a source of said power and control signals, said circuit lines terminating in printed circuit board connectors disposed at said other end proximal to said second widened portion of the elongated support plate.

5. The apparatus of claim 1, further comprising mechanical fluid couplings at an end thereof and distal from said first end of the elongated cylindrical portion, the mechanical fluid couplings respectively connectable to a fluid supply line and to a fluid discharge line for circulating fluid into and out of said apparatus.

6. The apparatus of claim 1, said apparatus configured to be magnetic field compatible allowing the apparatus to be used in a magnetic resonance imaging (MRI) treatment facility without substantially interfering with the operation of such magnetic imaging.

7. The apparatus of claim 6, said apparatus possessing a substantially radially symmetrical magnetic profile so that rotation of said apparatus during treatment within a magnetic imaging field would have little or no detrimental impact on magnetic imaging performed in conjunction with said treatment.

8. The apparatus of claim 1, wherein said transition portion is disposed between (a) first and second mechanical interfaces of said fluid conduit and (b) said second end, said first and second mechanical interfaces coupling intake and outtake connections, respectively, to respective fluid couplings that extend from said mechanical interfaces to said second end of said elongated cylindrical body.

9. The apparatus of claim 8, further comprising electrical couplings extending from said transition body portion to said second end of said elongated cylindrical body.

10. The apparatus of claim 1, wherein said transition body portion comprises an optically transparent material, said optically transparent material disposed and arranged to allow visual inspection of said fluid conduit.

11. The apparatus of claim 10, wherein said optically transparent material comprises a clear plastic.

12. The apparatus of claim 1, wherein said array of ultrasonic sources includes a first dummy source that is not electrically driven to provide thermal therapy in said patient, said first dummy source disposed at a first end of said array of ultrasonic sources.

13. The apparatus of claim 12, wherein said array of ultrasonic sources includes a second dummy source that is not electrically driven to provide thermal therapy in said patient, said second dummy source disposed at a second end of said array of ultrasonic sources.

* * * * *